United States Patent
Kim et al.

(10) Patent No.: US 10,252,030 B2
(45) Date of Patent: Apr. 9, 2019

(54) HANDHELD MAGNETIC GUN FOR GUIDE WIRE MANIPULATION

(71) Applicant: Cook Medical Technologies LLC, Bloomington, IN (US)

(72) Inventors: Woong Kim, West Lafayette, IN (US); Jarin Kratzberg, Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 230 days.

(21) Appl. No.: 15/408,046

(22) Filed: Jan. 17, 2017

(65) Prior Publication Data

US 2018/0200482 A1   Jul. 19, 2018

(51) Int. Cl.
| | |
|---|---|
| *A61M 25/01* | (2006.01) |
| *A61B 1/00* | (2006.01) |
| *A61B 34/00* | (2016.01) |
| *A61M 25/09* | (2006.01) |

(52) U.S. Cl.
CPC ..... *A61M 25/0127* (2013.01); *A61B 1/00158* (2013.01); *A61B 34/73* (2016.02); *A61M 2025/09116* (2013.01); *A61M 2025/09175* (2013.01); *A61M 2205/3317* (2013.01); *A61M 2205/3368* (2013.01); *A61M 2205/502* (2013.01); *A61M 2205/8206* (2013.01)

(58) Field of Classification Search
USPC .................................................. 361/139, 144
See application file for complete search history.

(56) References Cited

U.S. PATENT DOCUMENTS

| | | |
|---|---|---|
| 3,674,014 A | 7/1972 | Tillander |
| 5,216,400 A | 6/1993 | Leupold |
| 5,234,003 A | 8/1993 | Hall |
| 5,364,404 A | 11/1994 | Jaffe et al. |
| 5,654,864 A | 8/1997 | Ritter et al. |
| 5,706,827 A | 1/1998 | Ehr et al. |
| 5,906,579 A | 5/1999 | Vander Salm et al. |
| 6,014,580 A | 1/2000 | Blume et al. |

(Continued)

FOREIGN PATENT DOCUMENTS

| | | |
|---|---|---|
| CN | 201001771 Y | 1/2008 |
| CN | 102579088 A | 7/2012 |
| WO | WO 2010/129327 A1 | 11/2010 |

*Primary Examiner* — Danny Nguyen
(74) *Attorney, Agent, or Firm* — Brinks Gilson & Lione

(57) ABSTRACT

A magnetic field device for directing a magnetic coupling source includes an electrical power source, a control module, a muzzle, and an electromagnet adjacent the muzzle and connected to the electrical power source. A magnetic sensor within the muzzle is adjacent to the electromagnet. A magnet loading chamber is adjacent to the electromagnet magnetic and opposite to the magnetic sensor. The magnet loading chamber is configured to accommodate one or more permanent magnets. A magnetic shield surrounds exterior surfaces of the electromagnet and magnet loading chamber. A user operable control device is electrically connected to the electromagnet and to the electrical power source. The control device regulates an amount of electric current from the electrical power source to the electromagnet. A magnet guidewire delivery system includes a guide wire having a magnetic element and a magnetic field device generating a magnetic field that couples with the magnetic element.

17 Claims, 4 Drawing Sheets

(56) References Cited

U.S. PATENT DOCUMENTS

| | | | |
|---|---|---|---|
| 6,015,414 | A | 1/2000 | Werp et al. |
| 6,298,259 | B1 | 10/2001 | Kucharczyk et al. |
| 6,527,782 | B2 | 3/2003 | Hogg et al. |
| 6,902,528 | B1 | 6/2005 | Garibaldi et al. |
| 7,066,924 | B1 | 6/2006 | Garibaldi et al. |
| 7,335,170 | B2 | 2/2008 | Milne et al. |
| 7,727,269 | B2 | 6/2010 | Abraham-Fuchs et al. |
| 7,806,837 | B2 | 10/2010 | Rasmussen et al. |
| 7,815,580 | B2 | 10/2010 | Viswanathan |
| 7,914,493 | B2 | 3/2011 | Venbrux et al. |
| 9,049,987 | B2 | 6/2015 | Conlon et al. |
| 2004/0133130 | A1 | 7/2004 | Ferry et al. |
| 2005/0245846 | A1 | 11/2005 | Casey |
| 2006/0114088 | A1 | 6/2006 | Shachar |
| 2006/0270948 | A1 | 11/2006 | Viswanathan et al. |
| 2007/0021731 | A1 | 1/2007 | Garibaldi et al. |
| 2007/0197906 | A1 | 8/2007 | Ritter |
| 2008/0006280 | A1 | 1/2008 | Aliberto et al. |
| 2009/0209900 | A1* | 8/2009 | Carmeli .......... A61B 17/22012 604/22 |
| 2011/0245693 | A1* | 10/2011 | Hastings .............. A61B 5/0215 600/486 |
| 2011/0263925 | A1 | 10/2011 | Bratton |
| 2016/0022154 | A1 | 1/2016 | Warnking et al. |

\* cited by examiner

HANDHELD MAGNETIC GUN FOR GUIDE WIRE MANIPULATION

BACKGROUND

1. Technical Field Text

The disclosure relates to a magnetic field device for generating a magnetic field and directing a guide wire or a catheter and, more particularly, to a magnetic field device for directing an endovascular device, such as a guide wire, having a magnetically response element by application of the magnetic field.

2. Background

A typical endoluminal deployment system includes an inner catheter or cannula which may also be arranged as a pusher and/or dilator (hereinafter referred to as an inner catheter or catheter element) and a sheath covering the inner catheter. An implant or prosthesis is carried on the inner catheter and is fixed thereto by means of the covering sheath and with or without one or more restraining wires or any of a number of other known retention systems. The implant or prosthesis might be a stent, a stent graft, a filter, an occlusion device or any other implantable device of such a nature.

Once the distal end of the catheter has been positioned inside a patient, typically at the site of the patient's vasculature to be treated, the device is released and deployed in the desired position. The deployment operation involves retracting the covering sheath so as to expose the device to be implanted, which device is then deployed, either by self-expansion or by means of an expansion device such as an inflatable balloon. In the case where the device is also held by restraining wires, these are withdrawn, typically after retraction of the sheath. Restraining wires may or may not be used in such apparatus, generally dependent upon the nature of the device to be deployed, size restrictions and the particular medical application or intervention procedure.

In order to position a catheter at the site of the patient's vasculature to be treated, a guide wire is first inserted through the vasculature, for example, via the femoral artery. Once the guide wire is in position, a dimensioning catheter is passed over the guide wire to the site of treatment. The dimensioning catheter is provided with a plurality of gold marker bands and is used to determine the length of the vasculature that requires treatment. Once this has been determined, the dimensioning catheter is removed. The appropriate implant is then selected and delivered using a second catheter that is passed over the same guide wire. Typically, the positioning of the implant is achieved with X-ray analysis during the procedure.

Secondary cannulation of branching arterial vessels (renal, subclavian, common carotid) during bridging graft deployment is tedious and the longest process during the deployment. In this process, different catheters with various tortuosity are manually advanced to the target junction (with a guide wire) and tip of the catheter is manually rotated, pushed and/or pulled by hand ex situ until the catheter tip is successfully inserted to the branching artery. The challenge is that it is difficult to select optimal tortuosity via angiography and the rotation of catheter via wet-gloved fingers ex situ is extremely hard due to the small diameter and soft nature of the catheter material. For these reasons, cannulation process can take up to several hours, and is often a trial-and-error procedure that is highly dependent on the experience of the surgeon.

More recently, magnetically navigated guide wires and delivery catheters have been developed that can be controlled with the application of an external magnetic field. The guide wire or catheter includes a tip having a magnetic element responsive to an applied magnetic field. When the distal end of the guide wire is proximal to an arterial branch or bifurcation in the patients vasculature, the user operates a magnetic system outside of the patient to apply a magnetic field (often with the aid of a computerized user interface) to deflect the wire tip into an arterial branch. The magnet system can frequently direct the distal end of the guide wire into a vessel on a first effort, eliminating the trial and error of manually operated guide wires and thereby reducing or eliminating trauma to the vessel wall.

Currently available devices for applying a magnetic field are often large assemblies that are positioned over a patient and involve complex mechanical systems for holding the magnetic field generating unit and positioning the patient. Other systems are more compact and containing within a casing, but include complex positioning assemblies for adjusting the position of the magnetic field source assembly within casing. Thus, there existed a need for a magnetic field source with improved tactile manipulation for directing a magnetic catheter or guide wire through branching vasculature.

BRIEF SUMMARY

The present disclosure provides a magnetic field device for directing a magnetic coupling source, and a magnet guidewire delivery system that includes a magnetic field device and an endovascular device, such as a catheter and a guide wire having a magnetic element.

In one embodiment, a magnetic field device for directing a magnetic coupling source includes an electrical power source, a control module, a muzzle, and an electromagnet adjacent the muzzle and connected to the electrical power source. A magnetic sensor within the muzzle is adjacent to the electromagnet. A magnet loading chamber is adjacent to the electromagnet and opposite to the magnetic sensor. The magnet loading chamber is configured to accommodate one or more permanent magnets therein. A magnetic shield surrounding exterior surfaces of the electromagnet and magnet loading chamber. A user operable control device is electrically connected to the electromagnet and to the electrical power source. The control device is configured to regulate an amount of electric current from the electrical power source to the electromagnet.

In accordance with another embodiment, a magnet guidewire delivery system includes a guide wire having a magnetic element and a magnetic field device for generating a magnetic field. The magnetic field device includes an electrical power source, a control module, a muzzle, and an electromagnet adjacent the muzzle and connected to the electrical power source. A magnetic sensor within the muzzle is adjacent to the electromagnet magnetic. A magnet loading chamber is adjacent to the electromagnet and opposite to the magnetic sensor. The magnet loading chamber is configured to accommodate one or more permanent magnets therein. A magnetic shield surrounding exterior surfaces of the electromagnet and magnet loading chamber. A user operable control device is electrically connected to the electromagnet and to the electrical power source. The control device is configured to regulate an amount of electric current from the electrical power source to the electromagnet.

DETAILED DESCRIPTION

The magnetic field device and delivery system disclosed herein relates to a magnetic device that generates a directed magnetic field that couples with a magnet element positioned in an intravenous instrument, such as a guide wire, or a catheter, or the like. The magnetic device generates a magnetic field strength sufficient to couple with the magnet element, so as to direct a medical instrument positioned within the vasculature of a patient. In one embodiment, a guide wire has a ferromagnetic component at the tip that couples with the magnetic field produced by the magnetic device, such that the guide wire can be directed within the vasculature of a patent.

Figure 1:
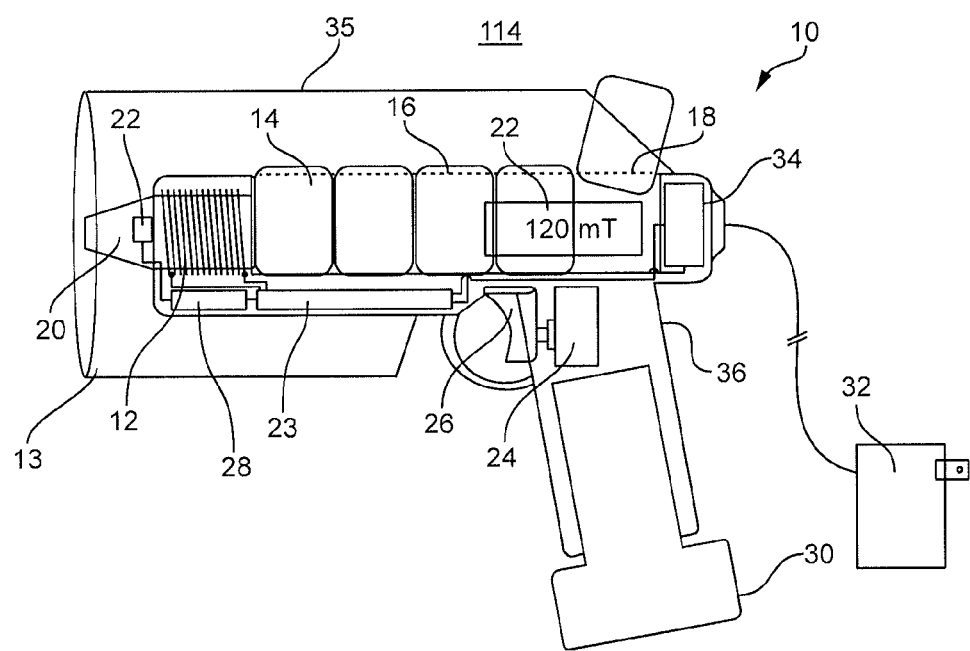
FIG. 1 illustrates a schematic drawing of a magnetic field device in accordance with an embodiment of the disclosed subject matter.

In an exemplary embodiment, a device for directing a magnetic field is configured as a hand-held magnetic field device 10, as illustrated in FIG. 1. The exemplary device is configured in the form of a magnetic gun fitted with an electromagnet 12 and a number of permanent magnets 14. In accordance with an aspect of the disclosed device, varying the number of permanent magnets enables the device to produce a varying magnetic field strength. As will subsequently be described, the magnetic force produced by the electromagnet 12 can be varied by the user. In combination with the electromagnet, a varying number of permanent magnets enable the magnetic force produced by the magnetic field device 10 to be adjusted by the user as necessary so as to manipulate guide wire or other intravenous device, for example, during cannulation of branching arterial vessels.

The permanent magnets 14 are sequentially inserted into a magnet chamber 16. The magnet chamber 16 has a closable opening 18 at the proximal end of the magnet chamber. A conductive plug of varying length (not shown) can be inserted as necessary in order for the permanent magnets to sit tightly together in magnet chamber. The permanent magnets are arranged to reside adjacent one another, such that the north and south poles of respective magnets are in contact with each other in a [N-S][N-S] arrangement.

In addition to the number of magnets, the magnetic strength of the permanent magnets can vary depending upon the particular desired magnetic strength to be generated by the magnetic field device 10. As will be subsequently described, the magnetic field device 10 must generate a sufficient magnetic field to magnetically couple with a magnetic element positioned in the vasculature of a patient. Accordingly, the magnetic field produced by the magnetic field device 10 must extend across body tissue of varying density and distance. In a preferred embodiment, the permanent magnets are commercially available neodymium magnets made from an alloy of neodymium, iron, and boron. The neodymium magnets preferably each have a weight of about 50 grams, however, other magnet weights can be used depending upon the particular physical attributes of the patient and the particular medical procedure being performed.

The magnetic field device 10 further includes a dome shaped muzzle 20 through which a magnetic field is concentrated and directed towards the magnet element in the medical device. The dome shaped muzzle 20 is preferably constructed from either ferromagnetic material or a permanent magnetic material, such that cumulative magnetic field is efficiently transferred to the body tissue of the patient.

A magnetic sensor 22 resides with in the dome shaped muzzle 20. The magnetic sensor 22 detects the strength of the magnetic field. In a preferred embodiment, the magnetic sensor 22 is a commercially available "giant magneto resistive" (GMR) device. One such GMR device is produced by NVE Corporation (Eden Prairie, Minn.) and is available as an AA analog sensor. As will subsequently be described, the magnetic sensor 22 is coupled to a display 22 that resides in sidewall of the device casing. In one embodiment, the display is a liquid crystal display (LCD) and the magnetic force generated at the muzzle 20 is shown on the display 22 in real-time, which provides quantitative information regarding the generated magnetic force to the user. The display 22 can also provide information generated by a controller regarding the approximate penetration depth of the magnetic field when given body weight of the patient. With the displayed information, the user can estimate the target magnetic field using the patient weight information.

Although as described and illustrated herein, the display is integrated into the magnetic field device 10, the display can optionally be housed in a separate unit connected by an electrical cable to the DC control module.

In cooperation with the permanent magnets 14, the strength of magnetic field produced by the magnetic field device 10 is controlled by a user operable control device 24. The device includes a variable switch 24 connected to a lever 26. In the illustrated embodiment, the lever 26 is shaped similar to a trigger of a firearm, such as a handgun. The control device 24 is operable by the user to increases or decreases current in the electromagnet 12. Operation of the control device 24 fine tunes the magnetic strength produced by the magnetic field device 10, such that guide wire, catheter, or other intravenous medical instrument can be manipulated within the vasculature. Fine adjustments in the generated magnetic strength are used by the surgeon to bend and relax the magnetic force at the magnetic element in the tip of a guide wire, for example. The magnetic strength can be controlled so as not to allow the tip of a medical device to pierce the vascular wall.

In accordance with an illustrative embodiment, the majority of static magnetic strength is provided by the number of permanent magnets 14 positioned in the magnet chamber 16, which is predetermined by the patient body weight.

In the illustrated embodiment, the magnetic field device 10 optionally includes a heat sensor 28. The heat sensor is positioned in proximity to the electromagnet 12 in order to monitor the amount of heat generated during operation of the device. The magnetic field device 10 is designed to dissipate heat efficiently such that several hours of continuous use does result in the generation of excessive heat. As will subsequently be described, heat sensor 28 is connected to a controller that is in-turn connected to the display 22. At the direction of the controller, a warning sign can be displayed and an audible alarm can be generated by a speaker (not shown) to alert the user. At a predetermined point in time after exceeding a predetermined threshold, the controller will cut off the current to the electromagnet 12.

The electrical power to the magnetic field device 10 can be provided by either a main battery 30 or by an AC adapter 32. The AC adapter 32 can be used to charge the main battery 30, while operating the magnetic field device 10 via a DC control module 34. The amount electrical charge is calculated by the processor 23 and battery status is displayed on the display 22.

While magnetic field generated by the magnetic field device 10 is preferably unidirectional, to prevent "missile effect" of anticipated ferromagnetic objects in proximity to the magnetic field device during operation, a magnetic shield 35 covers both the muzzle 20 and the large portions of the magnetic chamber 16. Preferably, the magnetic shield is composed of a metal, such as aluminum.

The components of the magnetic field device 10 described above are enclosed within a casing 36. The casing is preferably a plastic material that can be molded into a variety of shapes to accommodate the components and to provide ready manipulation of the magnetic field device 10 and the magnetic field produced by the device. In one embodiment, the casing is a molded ABS plastic. In the illustrated embodiment, the casing 36 of the magnetic field device 10 is molded in the familiar shape of a hand gun. The portion of the casing housing the main battery 30 is in the shape of a grip, while portion of the casing covering the magnet chamber 16 and the electromagnet 12 is in the shape of a gun barrel. As such, the shape of the casing 36 illustrated in FIG. 1 provides for ease in gripping the magnetic field device 10 and directing the magnetic field. In accordance with the invention, other shapes are possible, such as an elongated tube, a computer game controller, and the like.

Figure 2:
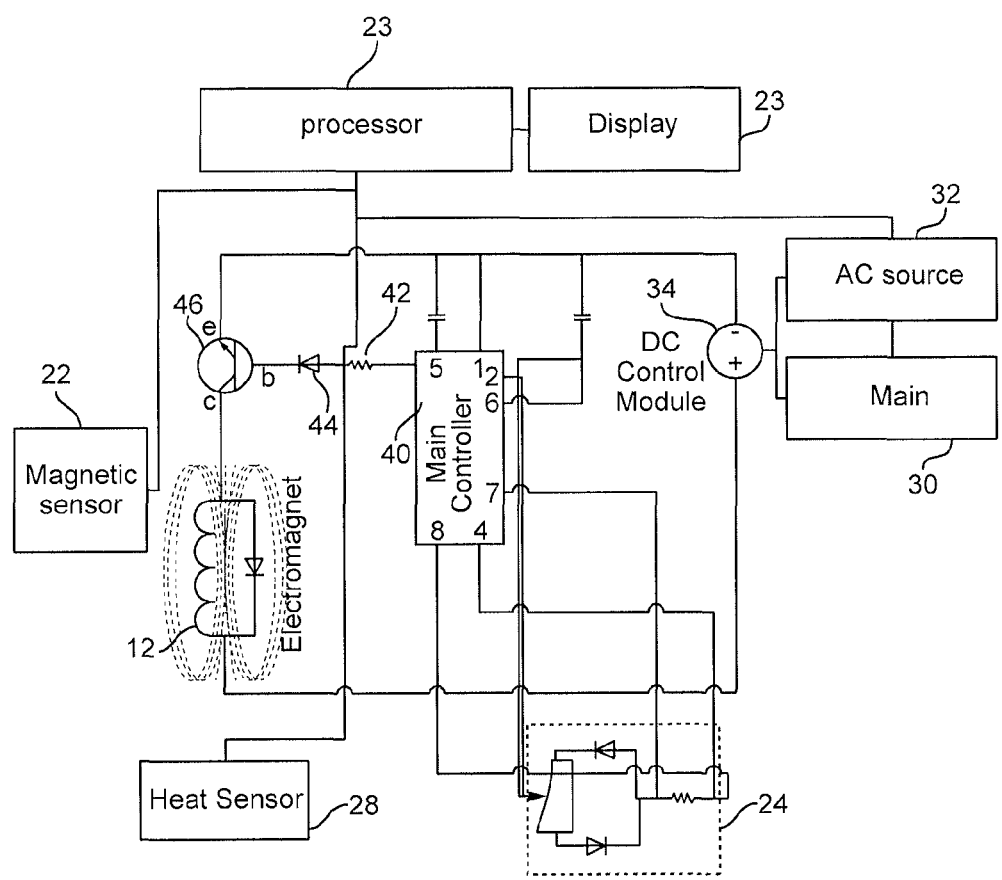
FIG. 2 illustrates a schematic diagram of the components and electrical connections of the magnetic field device of FIG. 1.

An exemplary circuit diagram of the magnetic field device 10 is illustrated in FIG. 2. A main controller 40 is connected to the variable switch 24, at connection pins 2, 4 and 8, and to the DC control module 34, at connection pin 1. The main controller 40 is also connected to the electromagnet 12, at connection pins 1 and 5, through a resistor, a diode 44, and a transistor 46. In one embodiment, the main controller 40 is preferably a conventional 555 Timer Integrated Circuit. In addition, the circuit incorporates the processor 23, which is connected to the magnetic sensor 22, the display 23, the heat sensor 28, the main battery 30, and the AC source 32. The component arrangement of the magnetic field device 10 is not limited to the particular configuration illustrated in FIG. 2. Other circuit arrangements are possible, including circuit configuration having a pulse width modulation (PWM) configuration that provide efficient use of electric current in variable power circuit.

Figure 3:
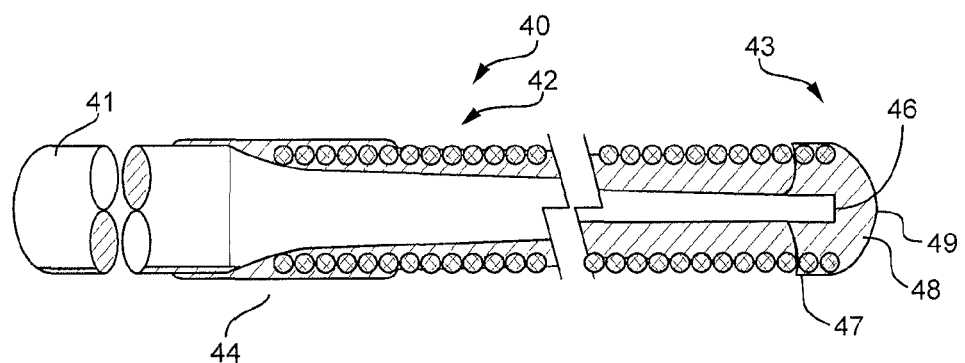
FIG. 3 illustrates a partially sectioned flexible tip wire guide having a magnetic element in accordance with one embodiment of the disclosed subject matter.

FIG. 3 illustrates an exemplary embodiment of a partially sectioned flexible tip wire guide 40 for a traumatic and controlled advancement through the vascular system of a patient. In particular, this flexible tip wire guide has a fracture resistant tip portion and is ideally suited for advancement through small, tortuous blood vessels such as the coronary vessels for positioning another medical device such as a guiding catheter thereover. The wire guide 40 includes elongated cylindrical wire member 41 having a main, uniform diameter portion that extends longitudinally nearly the entire length of the wire guide and a distal, decreasing diameter portion that distally and gradually increases in flexibility. A flexible wire coil 42 is positioned about the distal portion 43 and secured about a proximal end 44.

The flexible wire coil 42 is positioned over the distal portion 43 and secured thereto for presenting an increasingly flexible, a traumatic surface to a vessel wall. The coil 42 is preferably secured to the elongated cylindrical wire member about the distal and proximal ends for providing a substantially uniform outer diameter along the entire length of the wire guide 40 without weakening the elongated cylindrical wire member at the union with the coil.

A Distal end 46 of the wire member 41 is secured to a distal end 47 of the flexible coil 42 by a magnetic element 48 that can be either permanent magnet or any ferromagnetic material, such as magnetized stainless steel, iron or any other alloy suitable for endovascular application. The magnetic element 48 forms a hemispherical tip 49 and can extend up to about 3 mm from distal end 47 of the flexible coil. The outer diameter of the magnetic element 48 is preferably no larger than approximately 0.0185" so as to provide a uniform outer diameter along the length of the wire guide. Alternatively, the magnetic element 48 comprises a well-known weld, which typically includes melted stainless steel and platinum and is smaller in size than a silver solder tip.

The distal portion 43 of the wire guide can have a slight curve formed therein. This slight curvature allows the tip to be easily guided through a vessel by rotation of the wire guide. The distal portion can also be formed into a well-known J-tip configuration for directing the wire guide into branching vessels in a well-known manner by the attending physician. The cylindrical outer surface region is ideally suited for the straight distal tip portion of the J-tip configuration.

Figure 4:
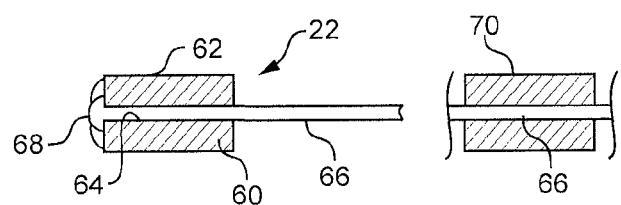
FIG. 4 illustrates a wire guide having one or more magnetic elements in accordance with another embodiment of the disclosed subject matter.

Another embodiment of a wire guide is illustrated in FIG. 4. A magnetic element 60 preferably has a cylindrical body 62 with an axial bore 64 therethrough. The distal end of the guide wire 66 extends through the bore 64, and is secured by a bead 68 of adhesive on the distal side of the magnetic element 60. The bead 66 provides a rounded head on the distal end of the guide wire. In accordance with another embodiment, the guide wire 66 can also have additional magnetic elements, such as magnetic element 70 attached thereto. By including additional magnetic elements along the length of the guide wire, additional bending and flexing of the guide wire can be obtained by exposure to the magnetic field generated by the magnetic field device 10.

EXAMPLE

Figure 5A:
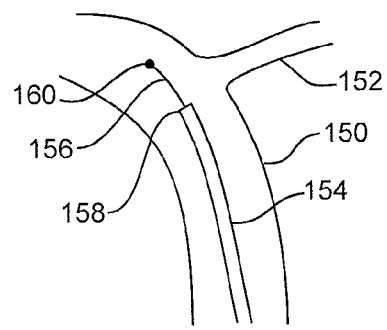
FIG. 5A illustrates a schematic diagram of a portion of an artery having a branching arterial vessel and a catheter and guide wire positioned inside the artery.

FIG. 5A illustrates a schematic diagram of a portion of an artery 150 having a branching arterial vessel 152. A catheter 154 is positioned inside the artery 150 and a guide wire 156 protrudes from a distal end 158 of the catheter 154. A magnet element 160 is attached to the distal tip of the guide wire 156. The catheter is advanced by a surgeon through the artery 150 and needs to further advance the catheter through the branching arterial vessel 152.

Figure 5B:
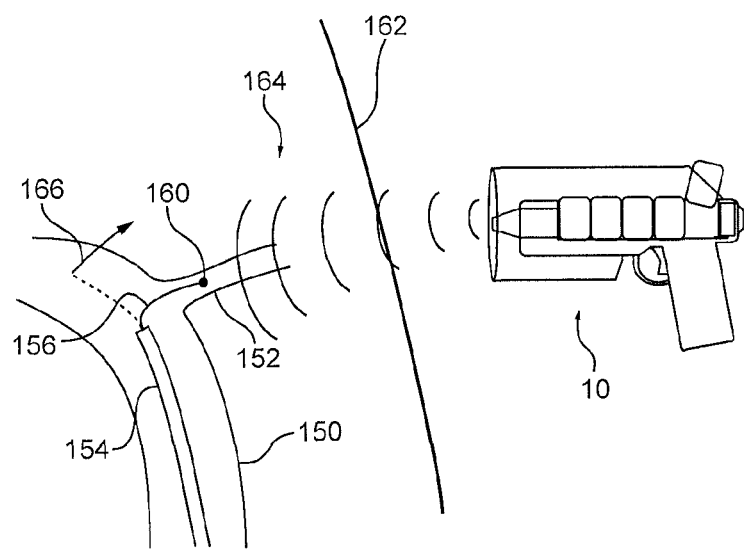
FIG. 5B illustrates the branching arterial vessel and the magnetic field device of FIG. 1 applying a magnetic field to drawn guide wire into the branching arterial vessel.

In accordance with a utility aspect of the invention, as illustrated in FIG. 5B, the surgeon positions the magnetic field device 10 in proximity to the skin surface 162 of a patient. The magnetic field device 10 is operated as described above to generate a magnetic field 164. The magnetic field couples with the magnet element 160 to draw the guide wire 156 in the direction shown by the arrow 166 and into the branching arterial vessel 52. As is known in the art, the progress of the guide wire 156 can be monitored by means of radio opaque sections of the guide wire 156 and the catheter 154.

In an exemplary method of use, if the patient weighs 100 kilogram, in exemplary application of the magnet device, the user will insert five 20 kilogram-strength, neodymium discs into the chamber. As such, the kilogram-strength of each permanent magnet inserted into the magnet chamber corresponds to the number of kilograms of patient body weight. The surgeon further estimates the approximate distance between the distal tip of the guide wire 156 at the arterial branching junction and the skin surface 162 of the patient, where the line of sight is aligned with the branching vessel. From this distance and the weight of the patient, the number of permanent magnets, each representing, for example, 1 inch (to provide 0.1 Tesla at the branch location) are inserted into the magnet chamber 16. The electromagnet 12, situated close to the muzzle 20, provides fine-tuning of the magnetic field intensity, while the permanent magnets provide additional magnetic attraction force to project the magnetic field through the patient's body tissue and draw the guide wire 156 into branching arterial vessel 152. In the example, approximate target magnetic field strength target is 0.1. Tesla. This magnetic field strength is suitable to bend and relax the guide wire tip, but is not strong enough cause the guide wire 156 to pierce the vascular wall lining. The magnetic field of the magnetic field device 10 is shielded by the magnetic shield 35, which surrounds the electromagnet and thereby shields a potential missile effect of other magnetically permeable items in the operating theater. Accordingly, secondary cannulation of the branching arterial vessel 152 is readily accomplished by use of the magnetic field device 10 and a guide wire equipped with the magnet element 60.

Thus, is apparent that there has been described magnetic field device and delivery system that fully provides the advantages set forth above. Those skilled in the art will recognize that numerous modifications and variations can be made without departing from the spirit and scope of the disclosed invention. For example, numerous casing configurations are possible physical including various grip configurations that provide for manipulation and precise aiming of the magnetic field generated by the device. Further, the magnetic field device can be configured to be mounted on a tripod or other support device. Accordingly, all such variations and modifications are within the scope of the appended claims and equivalents thereof.

The invention claimed is:

1. A magnetic field device for directing a magnetic coupling source, the device comprising:
   an electrical power source;
   a control module;
   a muzzle;
   an electromagnet adjacent the muzzle and connected to the electrical power source;
   a magnetic sensor within the muzzle and adjacent the electromagnet;
   a magnet loading chamber adjacent the electromagnet opposite the magnetic sensor, the magnet loading chamber configured to accommodate one or more permanent magnets therein;
   a magnetic shield surrounding exterior surfaces of the electromagnet and magnet loading chamber; and
   a user operable control device electrically connected to the electromagnet and to the electrical power source, the control device configured to regulate an amount of electric current from the electrical power source to the electromagnet.

2. The device of claim 1, wherein the user operable control device comprises a potentiometer coupled to the electromagnet through an intermediate a timing integrated circuit.

3. The device of claim 1, wherein the permanent magnets comprise neodymium magnets having north and south poles and residing adjacent one another, such that the north and south poles of respective magnets are in contact.

4. The device of claim 1, wherein the magnetic sensor comprises a giant magneto resistive (GMR) magnetic sensor.

5. The device of claim 1 further comprising a display, wherein the display is coupled to the magnetic sensor and configured to display a magnetic field strength produced by the device in proximity to the muzzle and detected by the magnetic sensor.

6. The device of claim 1, wherein the magnetic shield comprising an aluminum metal sheet material.

7. The device of claim 1 further comprising a DC control module.

8. The device of claim 7, wherein the electrical power source comprises a removable battery coupled to the DC control module.

9. The device of claim 7, wherein the electrical power source comprises an AC adapter coupled to the DC control module.

10. The device of claim 1 further comprising a heat sensor in proximity to the electromagnet and coupled to a display, the heat sensor configured to measure a temperature of at least the electromagnet during operation of the device.

11. A magnet guidewire delivery system comprising:
    a guide wire having a magnetic element; and
    a magnetic field device for generating a magnetic field, the device comprising:
      an electrical power source;
      a control module;
      a muzzle;
      an electromagnet adjacent the muzzle and connected to the electrical power source;
      a magnetic sensor within the muzzle and adjacent the electromagnet;
      a magnet loading chamber adjacent the electromagnet opposite the magnetic sensor, the magnet loading chamber configured to accommodate one or more permanent magnets therein;
      a magnetic shield surrounding exterior surfaces of the electromagnet and magnet loading chamber; and
      a user operable control device electrically connected to the electromagnet and to the electrical power source, the control device configured to regulate an amount of electric current from the electrical power source to the electromagnet.

12. The system of claim 11, wherein the guide wire further comprises:
    an elongated cylindrical wire member; and
    a flexible wire coil about a distal portion of the elongated cylindrical wire member,
    wherein a distal end of the cylindrical wire member is secured to a distal end of the flexible coil by the magnetic element.

13. The system of claim 12, wherein the magnetic element comprises a hemispherical tip comprising a magnetic material.

14. The system of claim 11, wherein the guide wire further comprises:
an elongated cylindrical wire member,
wherein the magnetic element comprises at least one cylindrical body with an axial bore therethrough, and the elongated cylindrical wire member extends through the axial bore.

15. The system of claim 14, wherein a distal end of the elongated cylindrical wire is secured to the at least one cylindrical body by a hemispherical bead.

16. The magnetic field device of claim 11 further comprising a display, wherein the display is coupled to the magnetic sensor and configured to display a magnetic field strength produced by the device in proximity to the muzzle and detected by the magnetic sensor.

17. The magnetic field device of claim 11 further comprising a heat sensor in proximity to the electromagnet and coupled to a display, the heat sensor configured to measure a temperature of at least the electromagnet during operation of the device.

* * * * *